United States Patent [19]

Koblitz et al.

[11] 4,411,625
[45] Oct. 25, 1983

[54] BROAD SPECTRUM LIGHT CURABLE DENTAL COMPOSITIONS

[75] Inventors: Franics F. Koblitz, York; Jane L. Reichart, Hanover, both of Pa.

[73] Assignee: Dentsply Research & Development Corp., Milford, Del.

[21] Appl. No.: 386,897

[22] Filed: Jun. 10, 1982

Related U.S. Application Data

[63] Continuation of Ser. No. 182,624, Aug. 29, 1980, abandoned.

[51] Int. Cl.³ .............................................. A61K 6/08
[52] U.S. Cl. ................................... 433/217; 106/35; 260/998.11; 433/199; 433/201; 433/202; 433/212; 433/222; 433/228; 523/115; 523/116; 523/117
[58] Field of Search ................. 106/35; 433/201, 168, 433/212, 217, 215, 226, 228; 260/998.11; 523/115-118

[56] References Cited

U.S. PATENT DOCUMENTS

| | | | |
|---|---|---|---|
| 3,254,411 | 6/1966 | Shelley | 32/15 |
| 3,488,269 | 1/1970 | Allen et al. | 204/159.23 |
| 3,677,920 | 7/1972 | Kai et al. | 204/159.15 |
| 3,709,866 | 1/1973 | Waller | 260/27 R |
| 3,759,809 | 9/1973 | Carlick et al. | 204/159.23 |
| 3,825,518 | 7/1974 | Foster et al. | 260/42.52 |
| 3,864,133 | 2/1975 | Hisamatsu et al. | 96/115 P |
| 3,954,584 | 5/1976 | Miyata et al. | 204/159.23 |
| 3,968,181 | 7/1976 | Uzelmeier et al. | 260/837 R |
| 4,065,587 | 12/1977 | Ting | 427/54 |
| 4,071,424 | 1/1978 | Dart et al. | 204/159.15 |
| 4,077,859 | 3/1978 | Costanza et al. | 204/159.23 |
| 4,089,762 | 5/1978 | Frodsham | 204/159.15 |
| 4,089,763 | 5/1978 | Dart et al. | 204/159.23 |
| 4,153,776 | 5/1979 | Friedlander et al. | 528/49 |
| 4,227,979 | 10/1980 | Humke et al. | 204/159.16 |

FOREIGN PATENT DOCUMENTS

| | | | |
|---|---|---|---|
| 12535 | 6/1980 | European Pat. Off. | 48/48 |

*Primary Examiner*—Lorenzo B. Hayes
*Attorney, Agent, or Firm*—Woodcock, Washburn, Kurtz, Mackiewicz & Norris

[57] ABSTRACT

Dental restorative composition are provided having improved color stability. According to a preferred embodiment, such compositions comprise a blend of a major proportion of inorganic, particulate filler, and a minor proportion of a resin component comprising a binder resin, a diluent monomer and a three part photosensitizing system comprising an alpha diketone, an amine reducing agent, and a benzoin alkyl ether. The superior color stability and other properties of restorative compositions of this invention are believed to result from synergistic interactions among the components of the sensitizing system.

3 Claims, No Drawings

BROAD SPECTRUM LIGHT CURABLE DENTAL COMPOSITIONS

This is a continuation, of application Ser. No. 182,624, filed Aug. 29, 1980, now patent.

BACKGROUND OF THE INVENTION

This invention provides composite dental restorative compositions which are curable by the action of light having visible and/or ultraviolet components. More particularly, formulations are disclosed which maintain good color stability and other beneficial physical properties while having the ease of workability attendant to light curable materials. These compositions employ broad spectrum photosensitizing systems having surprising synergistic superiority over either ultraviolet curing or visible light curing systems alone.

Dental restoratives should exhibit certain obligatory physical and chemical characteristics in order to be suitable for use in filling, repairing or replacing teeth. These restorative materials should possess properties that closely match natural teeth with respect to structural properties such as cohesive strength, coefficient of thermal expansion and wearability. Also, aesthetic considerations such as color stability, refractive index, plaque repellency, polishability and opacity are important factors in determining whether a material is suitable for use as a dental restorative. In the past, numerous organic composition have been tried in various mixtures and proportions in order to find satisfactory materials for use as dental composites or restoratives. These compositions have usually included some type of resin, which may either be preblended or mixed by the practitioner in the office, together with other materials such as pigments, catalysts, handling agents and opacifiers. For restorative use, it is generally necessary to employ materials which are "filled", that is, to which have been added amounts of inorganic, or in some cases, organic particulate material.

Composite or restorative materials should be distinguished from most film forming dental compositions. Such film forming materials provide resins containing minor or no substantial amounts of filler materials. They are frequently used as sealants, glazes, bonding agents, or adhesives. They may be used to coat a prepared tooth cavity prior to filling, thereby sealing off the tooth material against cracks and leaks adjacent to the filling. Such unfilled compositions have different viscosity requirements from dental composite materials because low viscosities are needed in the sealant materials in order to have proper flow characteristics. By contrast, dental composite and restorative materials must have good forming characteristics so that they can be shaped to fit a cavity area or molded into place in order to repair chipped or damaged teeth. Furthermore, such restorative compositions must preferably be filled with inorganic materials in order to achieve satisfactory hardness and durability during service.

It will be appreciated by those skilled in the art that the use of photoactivated materials is to be preferred over the more traditional thermochemical catalyst or redox activated systems because of the increased work time allowed by the use of photoinitiated polymerization. In a two component catalyst or redox system, work time is determined by the reaction time once the catalyst is added to the resin component. In a photocured system, the practitioner may take whatever time is necessary for forming or molding the dental restoration into formation and then effect extremely rapid curing by exposing the photocurable material to the appropriate wavelength of electromagnetic radiation.

Some prior art dental materials have utilized photoinitiators that are sensitive to ultraviolet radiation. There are, however, certain technical limitations which are present in ultraviolet-activated dental composite or restorative systems. For example, tooth structure attenuates ultraviolet radiation sufficiently so that it is not practical to cure ultraviolet-activated dental composites where direct access to the dental composite by the ultraviolet source is interfered with by intervening portions of tooth structure. Such is the case is classical undercuts used for mechanical retention of dental restorations. Ultraviolet-cured systems also cannot accomplish good depths of cure; stepwise restoration is frequently required.

It has been found that visible light having wavelengths from about 4000 angstroms to about 5000 angstroms is attenuated to a lesser degree by tooth structure than is ultraviolet radiation. Accordingly, it has been proposed to employ such visible light as the source of activating energy in dental compositions. Many previous attempts to develop restorative formulations using visible light curing systems have resulted in failure; such previous compositions have failed to exhibit one or more of the serviceability characteristics necessary for dental restoratives. A principal shortcoming is a lack of color stability and concomitant lack of aesthetic acceptability of the resulting products. Such a lack of color stability is a major shortcoming. The American Dental Association, the Internatinal Standards Organization, and others have developed detailed requirements for color stability in direct filling resins. See, for example, A.D.A. Specification No. 27; J.A.D.A. vol. 94, June 1977, pp. 1191–1194.

Accordingly, it is a principal object of this invention to provide compositions which are useful as dental restoratives. It is another object to provide such dental materials which exhibit improved color stability. Another object of this invention is to provide a one-component photocurable dental restorative system which is photocurable using light having ultraviolet and/or visible components. A further object is to provide dental compositions which exhibit a rapid cure time but which exhibit good workability prior to curing. Yet another object is to provide such compositions which exhibit improved shelf stability. A still further object is to provide dental compositions which are effective with lesser amounts of photoinitiators. Still other objects will become apparent from the following description of the invention.

DESCRIPTION OF THE PRIOR ART

It is to be understood that the term "bisphenol A" is commonly used in the art to indicate the chemical compound, 2,2-bis(4-hydroxyphenyl) propane. It is also to be understood that the term "bis-GMA" is commonly used to indicate the chemical compound, 2,2-bis[4-(2-hydroxy-3-methacryloxypropoxy) phenyl] propane, otherwise referred to as "diglycidyl methacrylate of bispenol A.".

U.S. Pat. No. 3,825,518 to Foster et al teaches dental filling materials which comprise a mixture of inorganic filler and the reaction product of an organic diisocyanate with a hydroxyalkyl acrylate or methacrylate to give a filled urethane diacrylate. A peroxide catalyst and a polymerization activator are employed.

U.S. Pat. No. 3,254,411 to Shelley teaches the use of a polyurethane liner to form a coating in the area of tooth to be filled. This liner acts as a sealant to prevent seepage of food particles and bacteria behind the filling that is to be placed in the tooth.

U.S. Pat. No. 3,488,269 to Allen et al teaches the use of visible light induced dye-redox initiated polymerization of vinyl monomers such as methacrylates. The improved initiators used here are characterized as having labile hydrogen.

U.S. Pat. No. 3,864,133 to Hisamatsu et al discloses photopolymerizable compositions which comprise a compound containing an ethylenically unsaturated double bond and urethane linkage and containing a secondary amino radical, a tertiary amino radical or a urea linkage. These materials are hardenable in the optional presence of air without the addition of wax. The materials formed are used in coating applications such as in wood sealers.

U.S. Pat. No. 3,759,809 to Carlick et al describes radiation curable compositions that have at least one isocyanatemodified polyfunctional ester with a hydroxyl value of about 15 to 70 used in conjunction with a photoinitiator. Reduced toxicity of these compounds is also noted. The primary use of these compounds is in lithographic inks.

U.S. Pat. No. 3,954,584 to Miyata et al teaches that certain photopolymerizable vinylurethane monomers are useful in the preparation of printing plates and reliefs. Actinic light having wavelengths of from 2000 to 5000 angstroms may be used depending on the species of the photosensitizers used. Photopolymerizable vinylurethane monomers are used in conjunction with a photo co-polymerizable ethylenically unsaturated liquid monomer, and a photosensitizer, with the vinylurethane monomer.

U.S. Pat. No. 4,065,587 to Ting utilizes UV curable poly(ether-urethane) polyacrylates for the formation of wet-look polymers. U.S. Pat. No. 3,968,181 to Uzelmeier teaches modified photocurable acrylate resins including bis-GMA. A UV sensitizer such as a benzoin ether may be employed. These materials are useful as coatings and adhesives. U.S. Pat. No. 4,153,776 to Friedlander et al discloses amide-modified urethane acrylate radiation curable compounds which are useful in film applications.

U.S. Pat. No. 4,071,424 to Dart et al teaches a photopolymerizable composition comprising at least one ethylenically unsaturated material and a photosensitive catalyst. Preferred photosensitizing systems employ alpha diketones with an amine reducing agent capable of being excited by radiation in the visible as well as in the UV region or both.

U.S. Pat. No. 4,089,762 to Frodsham teaches the use of a photopolymerizable composition comprising a polymerizable ethylenically unsaturated material, a photosensitizer of the structure which is preferably a diketone and a N-alkyl or N-cycloalkyl morpholine.

U.S. Pat. No. 4,089,763 to Dart et al teaches a method of repairing teeth using a composition which is curable by irradiation with visible light. These compositions include isocyanate modified bisphenol A derivatives in conjunction with a visible light sensitizing system.

U.S. Pat. No. 3,709,866 to Waller, assigned to the assignee of this invention, discloses the hexamethylene diisocyanate adduct of bis-GMA in a UV photocurable system. Benzoin methyl ether is employed as a UV activator. This disclosure is in part reflected in the commercial products NUVA-FIL, NUVA-FIL P.A., NUVA-SEAL, and NUVA-SEAL P.A. which are registered trademarks for past and present products of the L.D. Caulk Co.

SUMMARY OF THE INVENTION

It has been discovered that broad spectrum light polymerizable dental restorative compositions may be formulated having good physical characteristics together with improved color stability. Such dental compositions may comprise unitary or one-component blends of binder resin, diluent monomers, fillers and photoactivating or photosensitizing systems which are sensitive to visible and/or ultraviolet light. Such compositions may optionally be modified through the addition of restorative modificants such as pigments, stabilizers, opacifiers, etc. These materials are freely workable under ambient conditions until they are exposed to visible and/or ultraviolet light. At such time a rapid cure is effected to yield strong, durable, polishable dental restoratives with improved color stability.

DETAILED DESCRIPTION OF THE INVENTION

The compositions of this invention comprise broad spectrum polymerizable blends comprising binder resins, diluent monomers, fillers, and a broad spectrum photosensitizing system. Such blends may optionally include pigments, opacifiers, handling agents and other modificants as will be appreciated by those skilled in the art.

Binder resins suitable for use in the practice of one or more of the embodiments of this invention include a wide variety of ethylenically unsaturated polymerizable compositions. Preferably, such resins are selected from the class of acrylated polyesters. Thus, the bis-glycidylmethacrylate adduct of bisphenol A (bis-GMA) and its acrylic counterparts are preferred. Alternatively, the adducts of 2,2,3-trimethylhexane diisocyanate with hydroxyethyl methacrylate, hydroxypropyl methacrylate and other hydroxyalkyl acrylic species are also preferred. Those skilled in the art will appreciate that other acrylated polyesters may also be suitable. Such acrylated polyesters may also be reacted with isocyanates to form urethanes useful as binder resins. Thus, bis-GMA may be reacted with a diisocyanate (or other isocyanate) such as hexamethylene diisocyanate, phenylene diisocyanate or a wide variety of other aliphatic and aromatic diisocyanates to provide useful binder resins. The adducts of bis-GMA with hexamethylene diisocyanate have been found to be the best binder resin presently known for use in this invention.

The diluent monomer is added to the compositions of this invention in amounts sufficient to result in polymerizable formulations usually having viscosities between about 5,000 and about 70,000 centipoises, and preferably between about 40,000 and about 60,000 centipoises. Other viscosities may be employed for certain embodiments, however. Such viscosity control will be understood by those skilled in the art to result in moldable, workable, thixotropic materials suitable for a wide range of dental restorative uses. Diluent monomers may be any of a wide range of polymerizable monomers capable of sustaining a photochemically initiated polymerization. More preferably, such diluents may be the di-, tri- and higher acrylic species such as ethylene glycol dimethacrylate, diethylene glycol dimethacrylate, triethylene glycol dimethacrylate, etc., trimethylol propane trimethacrylate, analogous acrylates, and similar species.

While the components of the polymerized blend may be added in any order, it has been found useful and convenient to mix the binder resin and diluent together, to add the photosensitizing system components, and then to blend in the filler together with pigments and other modifying agents. In practice, the binder resin and diluent are mixed together in a proportion such that the final polymerizable composition will have the desired viscosity. While the relative amounts of binder resin and diluent will vary depending upon their identity and the type, size and amount of filler to be used, ratios of binder resin to diluent of from about 12:1 to about 1:2 and preferably, of from about 6:1 to about 1:1 are generally employed.

The photosensitizing system employed in the formulation of dental materials according to the practice of this invention comprises three components. An alpha diketone photosensitive species, (also known as an alpha, beta-diketone), an amine reducing agent and an ultraviolet photosensitizer selected from the family of benzoin alkyl ethers are employed. While any alpha diketone which is capable of initiating polymerization in the polymerizable systems of this invention may be employed, camphoroquinone, benzil, biacetyl, 9,10-phenanthrenequinone, and naphthoquinone have been found to be preferred. Most preferred is camphoroquinone.

Numerous amines have been found to be useful as reducing agents for inclusion in the present invention. Thus, amines such as tributylamine, tripropylamine and are useful. Still more useful are substituted amines such as N-alkyldialkanolamines and trialkanolamine. N-methyldiethanolamine is most preferred.

The ultraviolet light sensitizers suitable for inclusion in the formulations of this invention are selected from the chemical class of benzoin alkyl ethers. Thus, the methyl, ethyl, propyl, isopropyl, butyl, sec-butyl, isobutyl, tert-butyl, benzyl, etc. benzoin ethers may be employed. Benzoin methyl, ethyl, and isopropyl ethers have, to date, been found to be most preferred. Benzoin ketals such as benzoin dimethyl ketal and analogous species are also considered to be benzoin alkyl ethers.

The three-component photochemical sensitizing systems of this invention provide surprising advantages over the photochemical curing systems known to the prior art. More particularly, it is believed that combinations of benzoin alkyl ethers, alpha diketonic sensitizers and tertiary amines provide synergistic benefits to dental restorative compositions employing them. Thus, it is believed that benzoin alkyl ethers are storage stabilized when in combination with the other components of the three-component initiating system. As a result, it is possible to obtain sensitizing response in the ultraviolet spectrum from lesser quantities of benzoin alkyl ethers than can be obtained without such admixture in practical dental systems.

Additionally, it is believed that the benzoin alkyl ethers, especially the isopropyl and isobutyl ethers, interact when in combination with the alpha diketonic and amine species to form as yet unidentified interaction products which facilitate visible light curing. More particularly, it has been found that, when the three-components of the present dental restorative curing systems are combined, greater overall curing ability is demonstrated than would be expected from a combination of ultraviolet sensitizers alone and visible light sensitizers alone. As a result, significantly lower amounts of sensitizing agents may be employed to effect a particular degree of cure. Additionally, since the sensitizer levels appear to contribute in major degree to color instability in the dental resins employing them, the present system displays improved color stability as measured by A.D.A. specification number 27.

The properties of these dental restorative systems are believed to improve with ageing. Thus, ageing of the composite restoratives for from about 2 to about 30 days effects significant improvement in inter alia, curing rate.

The amount of alpha diketone photosensitizer is controlled to comprise from about 0.05% to about 0.30% by weight based upon the total weight of the binder resin, diluent monomer and photosensitizing system. It is even more preferred to employ from about 0.10% to about 0.25% of alpha diketone. The amount of amine reducing agent is less critical. It is useful to employ from about 0.2% to about 1.0% of amine with from about 0.3% to about 0.6% being preferred, based on the total weight of binder, diluent and photosensitizing system. A benzoin alkyl ether is included to the extent of from about 0.1% to about 1.0% with from about 0.2% to about 0.6% being preferred based on total weight of resin, diluent and photosensitizing system.

For the formulation of the broad spectrum light polymerizable compositions of this invention, the binder resin, diluent and photosensitizing system are blended together with fillers and, optionally but preferably, pigments and modificants. Those skilled in the art will appreciate that the amount of filler loading which may be accomplished with a given resinous system will depend upon several variables including the identity of the resins and fillers and the particle sizes of the fillers. It must be appreciated that, for a given resin formulation, judicious choice of filler type and filler particle size must be made. The filler used must be such that the transmission of visible and/or ultraviolet light by the restorative compositions is sufficient for polymerization to take place. Those skilled in the art will be able to select fillers and to determine filler particle sizes based upon this requirement.

Among those fillers which are especially suited for use in the practice of this invention are inorganic glasses. Preferred among these are barium aluminium silicate, lithium aluminium silicate, strontium, lanthanum, tantalum, etc. glasses, and related materials. Silica, especially in submicron sizes, quartz and other fillers may also be employed in some formulations. Such fillers are preferably silanated prior to use in the restoratives of this invention. Silanation is well known to those skilled in the art and any silanating compound known to them may be used for this purpose.

Fillers are selected having particle sizes which are, in general, less than about 50 microns. It is known that smaller sized filler particles result in highly polishable dental materials, but that the concomitant increase in surface area diminishes the overall filler loading possible with a given resin. Such lower loadings may be manifested by lesser degrees of strength, hardness, and durability in the resulting polymerized structures. It is possible to employ submicron sized fillers in some cases, however. The ratio of resin to filler employed for the practice of this invention must take account of the filler size as suggested above. In general, weight ratios of from about 10:90 to about 50:50 may be used, with from about 15:85 to about 30:70 being preferred.

Pigments, opacifiers, brightening agents, handling agents and other modificants may be included in the compositions of this invention without departing from its spirit.

The methods of use of the broad spectrum light curable compositions of this invention follow, to an extent, those currently practiced by those skilled in the art. Thus, the surface to be repaired is cleansed of decayed material and acid etched to promote bonding. At this point, a bonding agent may be employed by coating it upon the surface to be repaired. A material according to this invention is then molded into place in the conventional fashion. At this point, visible and/or ultraviolet light is directed onto the restorative material by any suitable source.

This exposure may take place directly or through one or more surfaces of tooth material due to the significant transmittance of tooth material to visible light. Following exposure, the restorative material undergoes polymerization. During this process, and afterward, the materials of this invention exhibit improved color stability as measured by A.D.A. Specification 27.

The following non-limiting examples further illustrate certain preferred embodiments of this invention.

EXAMPLE 1
BROAD SPECTRUM LIGHT CURABLE DENTAL RESTORATIVE

A resinous blend was formed from 19.0 g of the hexamethylene diisocyanate adduct of bis-GMA, 0.1 g of benzoin methyl ether, 0.02 g of camphoroquinone, and 0.06 g of N-methyldiethanolamine. To this resinous blend was added fillers and pigments comprising 78.08 g of Raysorb T-3000, a radiopaque barium glass filler sold by the Kimble Co., 0.64 g of silanated alumina, 1.52 g of iron oxide pigments and 0.76 g of Tullanox 300 which is a submicron silica offered by the Tulco Co. The resulting filled blend os useful as a composite or restorative and is curable by exposure to light spanning the visible and ultraviolet spectra. Such compositions exhibit good processing and physical characteristics for dental restorative use and exhibit improved color stability as measured by the A.D.A. Specification Number 27 color stability test. The composition of this example exhibits even better characteristics, especially higher rates of cure, after aging for from about 2 to about 30 days at 25° C.

EXAMPLE 2
POLYMERIZED DENTAL RESTORATIVES

The composition of Example 1 was exposed to light with wavelengths spanning the visible and ultraviolet spectrum. More particularly light with wavelengths between about 3,600 angstroms and 5,000 angstroms at a power of about 250 mw/cm$^2$ was employed. Exposure of the composition for about 20 seconds effected a depth of cure of about 2.8 mm. Longer exposures either directly upon the restorative or through tooth material enable depths of cure sufficient for all normal dental restorative techniques. The composition of Example 1 may be used for any of a wide range of dental restorative uses and exhibits good color stability, physical properties, and handling qualities.

EXAMPLE 3
DENTAL RESTORATIVE EMPLOYING MIXED FILLERS

A broad spectrum dental restorative employing microfine fillers was formulated as follows: a blend of 45.21 g bis-GMA, 11.30 g triethylene glycol dimethacrylate, 2.93 g bisphenol A dimethacrylate, 0.71 g phenyl salicylate, 1.11 g substituted benzophenones (the latter compounds serving as "hard" U.V. screens), 0.06 g butylated hydroxytoluene, 0.03 g iron oxide pigments, and 38.65 g of filler was prepared. The filler was a 60:40 mixture of approximately 0.05 micron silanated silica and approximately 2–5 micron milled silanated barium aluminium silicate. To 6 g of this blend was added 0.0019 g (0.1%) camphorquinone, 0.0056 g (0.3%) N-methyldiethanolamine and 0.0093 g (0.5%) benzoin methyl ether. Three grams of this activated blend was mixed with 4 g of additional filler to provide a broad spectrum curable restorative having sensitivity to both ultraviolet and visible light. Allowing this composition to age 2–30 days improved its performance.

What is claimed:

1. A process for repairing teeth comprising applying to a prepared tooth a dental restorative composition curable by irradiation by visible and/or ultraviolet light comprising
   a major proportion of an inorganic filler, and
   a minor proportion of a resin component comprising:
   a binder resin, comprising bis-GMA reacted wtih aliphatic diisocyanate,
   a polymerizable acrylic diluent monomer, and
   a photosensitizing system comprising from about 0.05% to about 0.30% by weight of the restorative of an aliphatic alpha diketone,
   from about 0.2% to about 1.0% by weight of the restorative of an amine reducing agent, and
   from about 0.1% to about 1.0% by weight of the restorative of a benzoin alkyl ether,
   said photosensitizing system being present in an amount sufficient to cause substantial polymerization of said composition upon irradiation with visible and/or ultraviolet light,
said composition retaining good color stability, and exposing said composition to visible and/or ultraviolet light for a time sufficient to cause substantial polymerization of said composition.

2. The process of claim 1 wherein said light has substantial components in both the ultraviolet and visible spectra.

3. The process of claim 1 wherein said diketone is camphorquinone.

* * * * *